United States Patent [19]

Karami

[11] 4,047,530
[45] Sept. 13, 1977

[54] DISPOSABLE DIAPER WITH FASTENER RETAINED END BARRIER

[75] Inventor: Hamzeh Karami, Crystal Lake, Ill.

[73] Assignee: Colgate-Palmolive Company, New York, N.Y.

[21] Appl. No.: 715,785

[22] Filed: Aug. 19, 1976

[51] Int. Cl.$^2$ ............................................. A61F 13/16
[52] U.S. Cl. .................... 128/287; 128/284; 128/290 R
[58] Field of Search ................... 128/287, 284, 290 R

[56] References Cited

U.S. PATENT DOCUMENTS

| 2,714,889 | 8/1955 | Chambers | 128/287 |
| 3,089,494 | 5/1963 | Schwartz | 128/284 |
| 3,150,664 | 9/1964 | Noel | 128/287 |
| 3,646,937 | 3/1972 | Gellert | 128/287 |
| 3,978,861 | 9/1976 | Schaar | 128/287 |

Primary Examiner—Aldrich F. Medbery
Attorney, Agent, or Firm—Powell L. Sprunger

[57] ABSTRACT

A disposable diaper comprising, an absorbent pad assembly having a pair of side edges, a pair of end edges connecting the side edges, a front surface, a backing sheet of fluid impervious material defining a back surface of the pad assembly, an absorbent pad, and a laterally extending end section including the backing sheet adjacent one end edge of the pad assembly. The end section is folded along a fold line with a front surface of the end section facing the front surface of an underlying portion of the pad assembly adjacent the fold line. The diaper has a tape fastener comprising, a release sheet having a release back surface and having a first end portion secured to the back surface of the end section and a second end portion secured to the back surface of the pad assembly and spaced from the end section, with the release sheet retaining the end section in its overlying configuration. The fastener has a pressure-sensitive tape strip having a first portion secured to the diaper adjacent the second portion of the release sheet, and a second securement portion releasably attached to the release surface in the first end portion of the release sheet. The securement portion of the tape strip is removed from the release sheet to secure the diaper about the infant.

5 Claims, 6 Drawing Figures

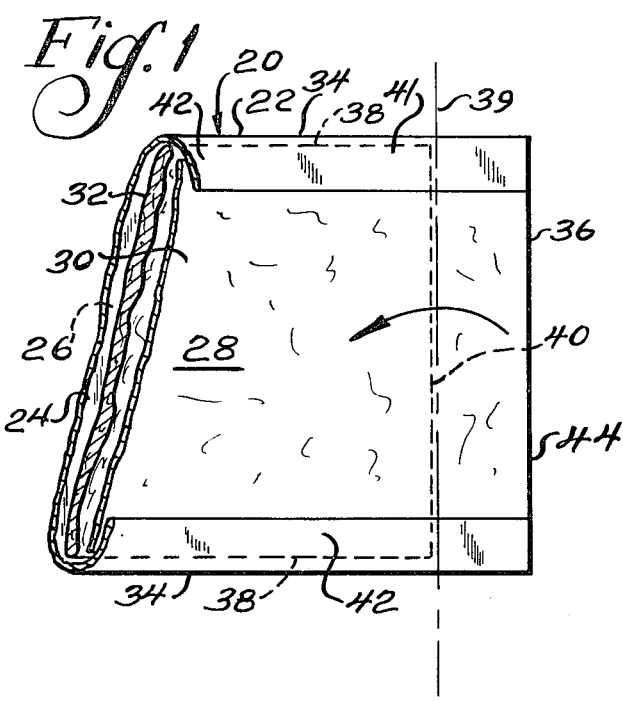
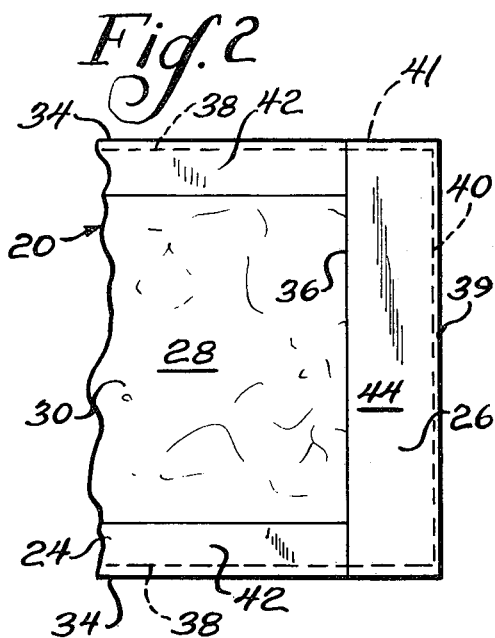
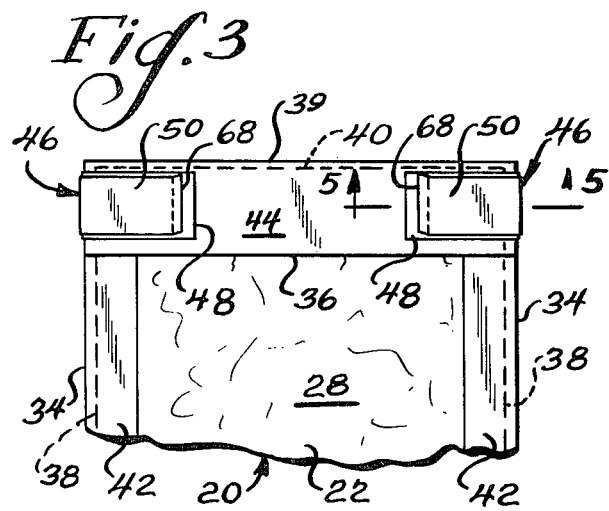
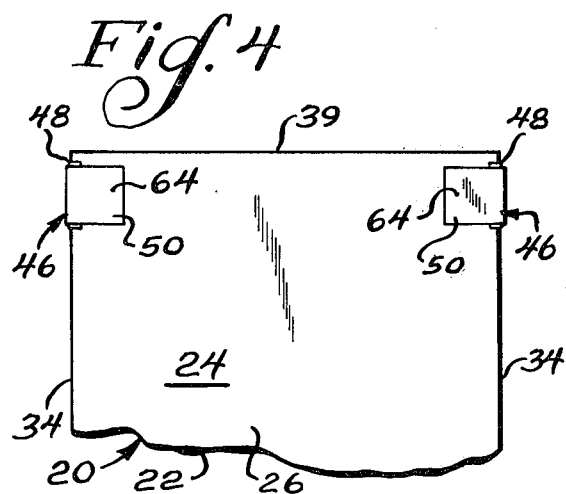
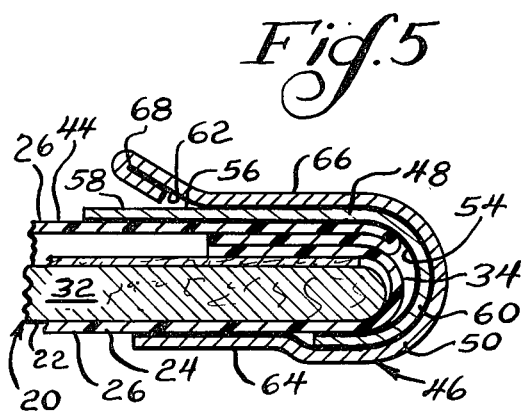
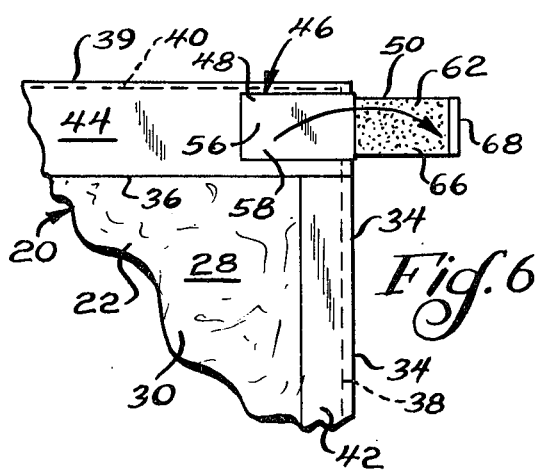

DISPOSABLE DIAPER WITH FASTENER RETAINED END BARRIER

BACKGROUND OF THE INVENTION

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets. The diapers have also been provided with tape fasteners normally having a securement portion having adhesive covered with a release sheet.

One of the problems associated with such diapers has been recurrent leakage from the absorbent pad in the waistline portion. Further, it is desirable that the release sheets of such fasteners are not separated from the diaper when removed from the securement portions, since such loose release sheets must be discarded by the parents during placement of the diaper, thus causing inconvenience of necessary disposal.

SUMMARY OF THE INVENTION

A principal feature of the present invention is the provision of a disposable diaper which minimizes leakage from an end of the diaper during use.

The diaper of the present invention comprises, an absorbent pad assembly having a pair of side edges, a pair of end edges connecting the side edges, a front surface, a backing sheet of fluid impervious material defining a back surface of the pad assembly, an absorbent pad, and a laterally extending end section including the backing sheet adjacent one end edge of the pad assembly. The end section is folded along a lateral fold line with a front surface of the end section facing the front surface of an underlying portion of the pad assembly adjacent the fold line. The diaper has a tape fastener comprising, a release sheet having a release back surface and having a first end portion secured to the back surface of the end section and a second end portion secured to the back surface of the pad assembly and spaced from the end section. The fastener also has a pressure-sensitive tape strip having a first portion secured to the diaper adjacent the second portion of the release sheet, and a second securement portion releasably attached to the release surface in the first end portion of the release sheet, with the securement portion of the tape strip being removed from the release sheet to secure the diaper about the infant.

A feature of the present invention is that the release sheet retains the end section in its overlying configuration of the pad assembly.

Another feature of the present invention is that the end section overlies an end portion of the absorbent pad.

Thus, a feature of the present invention is that the fluid impervious backing sheet in the retained end section provides a barrier to prevent fluid leakage from the end of the absorbent pad.

Still another feature of the invention is that the end section is retained in its overlying configuration through use of the tape fastener and without additional securement means.

Yet another feature of the invention is that the tape fastener eliminates the necessity of discarding separate release sheets during placement of the diaper.

Further features will become more fully apparent in the following description of the embodiments of this invention and from the appended claims.

DESCRIPTION OF THE DRAWINGS

In the drawings:

FIG. 1 is a fragmentary front plan view of a disposable diaper;

FIG. 2 is a fragmentary front plan view of the diaper of FIG. 1 illustrating an end section of a pad assembly in the diaper as folded over the pad assembly;

FIG. 3 is a fragmentary front plan view of a pair of tape fasteners utilized to retain the end section in its folded configuration;

FIG. 4 is a fragmentary back plan view of the diaper of FIG. 3;

FIG. 5 is a fragmentary sectional view taken substantially as indicated along the line 5—5 of FIG. 3; and FIG. 6 is a fragmentary front plan view of the diaper of FIG. 3 illustrating a securement section of the tape fastener being folded into a configuration for securing the diaper about an infant.

DESCRIPTION OF THE PREFERRED EMBODIMENTS

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly 22, a fluid pervious cover or top sheet 28, such as a nonwoven material, defining a front surface 30 of the pad assembly 22, and an absorbent pad 32 located intermediate the backing sheet 24 and top sheet 28. As shown, the pad assembly has a pair of side edges 34, and end edges 36 connecting the side edges 34. The absorbent pad 32 also has a pair of side edges 38 and end edges 40 connecting the side edges 38. In a preferred embodiment, as shown, the end edges 40 of the absorbent pad 32 are spaced from the end edges 36 of the pad assembly 22, and the side edges 38 of the absorbent pad 32 are located adjacent the side edges 34 of the pad assembly 22. The backing sheet 24 has lateral side margins 42 folded over and secured to the top sheet 28, such that the side margins 42 of the backing sheet 24 cover lateral side margins of the absorbent pad 32.

The pad assembly has an end section 44 in a waistline portion of the diaper. The end section 44 includes an end portion of the backing sheet 24 which is folded along a lateral fold line 39 with the end section 44 overlying the front of the diaper. Thus, the front surface 30 of the end section 44 faces the front surface of an underlying portion 41 of the pad assembly 22 adjacent the fold line 39, such that the back surface 26 of the end section 44 faces outwardly from the front of the diaper. In a preferred form, as shown, the fold line 39 is located adjacent the end edge 40 of the absorbent pad 32, and is located intermediate the end edge 40 of the absorbent pad 32 and the end edge 36 of the pad assembly 22. In the folded over configuration, the end section 44 thus overlies an end margin of the absorbent pad 32, and the fluid impervious backing sheet in the end section 44 provides a fluid impervious barrier at the end of the absorbent pad to prevent leakage from the absorbent pad of the pad assembly during use of the diaper.

With reference to FIGS. 3-5, the diaper 20 also has a tape fastener generally designated 46. The tape fastener has a release sheet 48 and a pressure-sensitive tape strip 50. As best shown in FIG. 5, the release sheet 48 has adhesive 54 on a front surface and a release back surface 56. The adhesive 54 on a first end section 58 of the release sheet 48 is secured to the back surface 26 of the end section 44, and the adhesive 54 on a second end section 60 of the release sheet 48 is secured to the back surface 26 of the pad assembly 22 at a location spaced from the end section 44 across the fold line 39. Thus, the opposed ends 58 and 60 of the release sheet 48 are secured between the end section 44 and the adjacent portion 41 of the pad assembly on opposed sides of the fold line, and, in this manner, the release sheet 48 retains the end section 44 of the pad assembly in its folded over configuration to prevent leakage from the absorbent pad 32. Accordingly, the end section 44 of the pad assembly 22 is retained in its folded configuration without the necessity of additional securing means, such as separate spots or lines of adhesive.

The tape strip 50 has adhesive 62 on a front surface, and the adhesive 62 on a first end portion 64 of the tape strip 50 is attached to the back surface 26 of the pad assembly 22 adjacent the second end section 60 of the release sheet 48. As shown, a second securement end portion 66 of the tape strip 50 is folded over the release sheet 48, such that the adhesive 62 of the securement portion 66 is releasably attached to the release surface 56 of the first end section 58 of the release sheet 48. The tape strip 50 may have a folded over portion 68 at its outer end defining a tab to facilitate removal of the securement portion 66 of the tape strip 50 from the release sheet 48. In use, the tab is used to remove the securement portion 66 of the tape strip 50 from the release sheet 48, and the securement portion 66 is folded into a position extending past the side edge 34 of the pad assembly 22, as shown in FIG. 6. In this configuration, the securement portions 66 of the tape fasteners 46 are utilized to secure the diaper about the infant by attaching the securement portions 66 to spaced portions of the diaper. Thus, the release sheets 48 remain attached to the pad assembly while retaining the end section 44 in its folded over configuration, and the tape fasteners 46 eliminate the necessity for discarding separate release sheets during placement of the diaper.

The foregoing detailed description is given for clearness of understanding only, and no unnecessary limitations should be understood therefrom, as modifications will be obvious to those skilled in the art.

I claim:

1. A disposable diaper, comprising:
an absorbent pad assembly having a pair of side edges, a pair of end edges connecting the side edges, a front surface, a backing sheet of fluid impervious material defining a back surface of the pad assembly, an absorbent pad, and a laterally extending end section including the backing sheet adjacent one end edge of the pad assembly, said end section being folded along a lateral fold line with a front surface of the end section facing the front surface of an underlying portion of the pad assembly adjacent said fold line; and
a tape fastener comprising, a release sheet having a release back surface and having a first end portion secured to the back surface of said end section and a second end portion secured to the back surface of the pad assembly and spaced from said end section, with said release sheet retaining the end section in its overlying configuration, said fastener having a pressure-sensitive tape strip having a first portion secured to the diaper adjacent said second portion of the release sheet, and a second securement portion releasably attached to the release surface in the first end portion of the release sheet, said securement portion of the tape strip being removed from the release sheet to secure the diaper about the infant.

2. The diaper of claim 1 wherein said end section overlies said absorbent pad.

3. The diaper of claim 1 wherein said fold line is located adjacent an end edge of the absorbent pad.

4. The diaper of claim 3 wherein said fold line is located intermediate the end edge of the pad and said one end edge of the pad assembly.

5. The diaper of claim 1 wherein said securement portion of the tape strip includes tab means at an outer end thereof.

* * * * *